(12) United States Patent
Peuker et al.

(10) Patent No.: US 11,806,204 B2
(45) Date of Patent: Nov. 7, 2023

(54) SELF-RESEALING MAGNET CLOSURE

(71) Applicant: 3M INNOVATIVE PROPERTIES COMPANY, St. Paul, MN (US)

(72) Inventors: Marc Peuker, Schondorf (DE); Andreas J. Boehm, Reichling (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 142 days.

(21) Appl. No.: 17/309,241

(22) PCT Filed: Nov. 21, 2019

(86) PCT No.: PCT/IB2019/060049
§ 371 (c)(1),
(2) Date: May 11, 2021

(87) PCT Pub. No.: WO2020/115598
PCT Pub. Date: Jun. 11, 2020

(65) Prior Publication Data
US 2021/0393373 A1  Dec. 23, 2021

(30) Foreign Application Priority Data

Dec. 3, 2018  (EP) .................................. 18209732

(51) Int. Cl.
*A61C 5/62* (2017.01)
*A61C 5/64* (2017.01)
(Continued)

(52) U.S. Cl.
CPC .............. *A61C 5/64* (2017.02); *A61M 39/20* (2013.01); *A61C 2201/00* (2013.01)

(58) Field of Classification Search
CPC ........... A61C 9/0026; A61C 5/62; A61C 5/64; B65D 81/325; B65D 2313/04;
(Continued)

(56) References Cited

U.S. PATENT DOCUMENTS 4,983,379 A * 1/1991 Schaeffer ................. A61K 8/42
424/53
4,989,758 A * 2/1991 Keller .................. B65D 81/325
222/137
(Continued)

FOREIGN PATENT DOCUMENTS

CN 201999305 10/2011
CN 104373602 2/2015
(Continued)

OTHER PUBLICATIONS

Extended EP Search Report for EP Application No. 18209732.9, dated Apr. 26, 2019, 2 pages.
(Continued)

*Primary Examiner* — Jacqueline T Johanas
*Assistant Examiner* — Zachary Alexander Kim (57) ABSTRACT

A syringe for dispensing a flowable material. The syringe has a cartridge with a cartridge front end and at least a first dispensing nozzle arranged at the cartridge front end. The syringe further has closure for openably closing the first dispensing nozzle. The closure includes a cap and at least a first seal. The cap is telescopically placeable on the cartridge front end. The closure or the cartridge has a first magnet for establishing a magnetic attraction between the closure and the cartridge. In a situation in which the closure is placed on the cartridge front end, the closure and the cartridge can be positioned in a sealing position in which the first seal spaces the cap and the cartridge front end away from each other against a magnetic attraction that urges the cap and the cartridge toward each other.

12 Claims, 3 Drawing Sheets

(51) Int. Cl.
*A61M 5/178* (2006.01)
*A61M 39/20* (2006.01)

(58) Field of Classification Search
CPC ...... B65D 41/00–41/62; B65D 45/00–45/345;
B65D 51/00–51/32; B65D 35/10; B65D
35/22; B65D 35/38; B65D 35/242; B65D
41/026; A61M 5/178; A61M 3/005;
A61M 35/20; B05C 17/00593; B05C
17/00559; A91M 5/19; A61J 1/1412;
A61J 7/0053
See application file for complete search history.

(56) References Cited

U.S. PATENT DOCUMENTS

| | | | | |
|---|---|---|---|---|
| 5,033,650 | A * | 7/1991 | Colin | B05C 17/00593 |
| | | | | 285/361 |
| 5,439,131 | A * | 8/1995 | Kato | B65D 47/0885 |
| | | | | 220/264 |
| 5,624,410 | A * | 4/1997 | Tsukada | B65D 47/14 |
| | | | | 220/230 |
| 5,735,437 | A * | 4/1998 | Broyles | A61C 5/62 |
| | | | | 222/391 |
| 9,179,647 | B2 * | 11/2015 | Lambert | A01K 27/001 |
| 2005/0192535 | A1 * | 9/2005 | Takagi | A61M 25/0618 |
| | | | | 604/164.08 |
| 2011/0066107 | A1 * | 3/2011 | Stephens | A61M 5/3202 |
| | | | | 604/110 |
| 2011/0306937 | A1 | 12/2011 | Andreoni | |
| 2014/0061199 | A1 * | 3/2014 | Dalbec | B65D 51/24 |
| | | | | 53/471 |
| 2014/0263319 | A1 * | 9/2014 | Fazi | B65D 51/00 |
| | | | | 220/230 |
| 2015/0125827 | A1 | 5/2015 | Claypool | |
| 2017/0086580 | A1 * | 3/2017 | Conti | A47G 23/02 |
| 2017/0265618 | A1 * | 9/2017 | Eberlein | A45D 34/045 |
| 2017/0296121 | A1 * | 10/2017 | Dar | A61N 1/0484 |
| 2018/0339113 | A1 | 11/2018 | Wendland | |
| 2019/0263568 | A1 * | 8/2019 | De Rosa | B65D 41/023 |

FOREIGN PATENT DOCUMENTS

| | | |
|---|---|---|
| CN | 105073162 | 11/2015 |
| CN | 106267471 | 1/2017 |
| CN | 207242501 | 4/2018 |
| CN | 108349633 | 7/2018 |
| EP | 2394685 | 12/2011 |
| EP | 3173157 | 5/2017 |
| TW | 201333353 A | 8/2013 |
| WO | WO 1989-008468 | 9/1989 |
| WO | WO 1997-027000 | 7/1997 |
| WO | WO 2017-180545 | 10/2017 |

OTHER PUBLICATIONS

International Search Report for PCT International Application No. PCT/IB2019/060049, dated Jan. 3, 2020, 5 pages.

* cited by examiner

SELF-RESEALING MAGNET CLOSURE

CROSS REFERENCES TO RELATED APPLICATIONS

This application is a national stage filing under 35 U.S.C. 371 of PCT/IB2019/060049, filed Nov. 21, 2019, which claims the benefit of European Application No. 18209732.9 filed Dec. 3, 2018, the disclosure of which is incorporated by reference in its/their entirety herein.

FIELD OF THE INVENTION

The invention relates to a syringe for dispensing a flowable material. In particular the invention relates to a syringe having a cartridge that can be sealed by a closure that is retained on the cartridge by magnetic attraction that continues to urge the closure onto the cartridge so that a seal or seals provided in the closure are kept pressurized over time.

BACKGROUND

Dental materials are often provided in syringes that have a cartridge or barrel forming a chamber for storing a dental material, and a piston or plunger for expelling the dental material from a dispensing nozzle of the chamber. Dental materials that are provided "ready to use" are typically provided in the in a single component syringe that has a single chamber with a dispensing nozzle and one piston for extruding the dental material from the chamber.

Some dental materials are provided in the form of two or more components that are stored separate from each other and mixed just before use. Such multi-component dental materials may be provided in a syringe that has a chamber for each component. There are a variety of syringes for storing and dispensing dental materials that are provided in the form of two or more components.

As a common requirement, one, two or multi-component dental materials typically have to be stored in the absence of air and/or encapsulated from the environment. Therefore many syringes are provided with a closure, for example a cap, for closing and sealing the dispensing nozzle or nozzles before use and often also between several uses.

For example, US 2015/125827 A1 (Claypool et al.) discloses a viscous paste dispensing apparatus that includes a barrel, a plunger assembly and a cap. Further, WO 97/27000 A2 (3M) discloses a dispenser containing a dental material to be dispensed in the form of two components stored in two chambers that each have an outlet. The dispenser further includes a cap that is detachably connected to the outlet.

US 2011/306937 A1 (Andreoni et al.) describes a magnetic safety needle assembly including a hub, a needle fixed to the hub, a shield movable relative to said hub, a first magnetic element fixed to said hub and a second magnetic element fixed to said shield, wherein said first and second magnetic elements are configured so as to define a repulsive force therebetween.

It is generally desirable, that the cap of a syringe helps ensuring that the dental material stays hermetically sealed during storage.

Although existing syringes are often provided with a cap that is designed to tightly seal an outlet of the syringe there is still a desire to ensure the tight seal also between multiple uses of the same syringe.

SUMMARY OF THE INVENTION

The invention concerns a syringe for dispensing a flowable material. Although a preferred use of the syringe is within the field of the preparation of a dental material, the flowable material may be a dental material, an adhesive or a sealant. In particular the flowable material may be a hardenable material, for example a hardenable dental material, a hardenable adhesive or a hardenable sealant.

The syringe comprises a cartridge having a cartridge front end with at least a first dispensing nozzle. Further, the syringe comprises a closure for openably closing the first dispensing nozzle.

The closure comprises a cap and at least a first seal. The cap, and thus preferably the closure, is telescopically placeable on the cartridge, in particular on the cartridge front end.

One of the closure and the cartridge has a first magnet for establishing a magnetic attraction between the closure and the cartridge. For example the cartridge may have a first magnet for establishing a magnetic attraction between the closure and the cartridge.

In a situation in which the closure is placed on the cartridge front end, the first seal is arranged between the cap and the first dispensing nozzle, with the closure and the cartridge being positionable in a sealing position in which the first seal spaces the cap and the cartridge front end away from each other against a magnetic attraction that urges the cap and the cartridge toward each other.

Preferably, the cartridge extends along a longitudinal axis. Further, preferably the telescopic placement of the closure on the cartridge (or cartridge front end) includes a movement of the closure and the cartridge toward each other along the longitudinal axis.

The wording "the first seal spaces the cap and the cartridge front end away from each other against a magnetic attraction that urges the cap and the cartridge toward each other" further means that (in absence of a second or further seal) if the first seal would not be present, the cap would move further toward the cartridge front end. In other words (in absence of a second or further seal) only the presence of the first seal prevents the cap and the cartridge front end to further move toward each other.

The invention is advantageous in that it provides a syringe that is easy and reliable in use. In particular the invention provides a syringe having a self-sealing and a self-resealing function. This means that the syringe of the invention allows a user to place the closure on the cartridge to an approximate position from which the closure is further pulled into the sealing position in a self-acting manner by magnetic attraction. Accordingly the invention helps minimizing failures from inaccurately placing the closure onto the cartridge. In particular, situations in which the closure appears to be positioned in the sealing position but actually it is not entirely positioned in the sealing position can be avoided. Further, once the closure and the cartridge are positioned in the sealing position. The syringe allows the closure and the cartridge to re-adjust into a new sealing position in case the seal shrinks or otherwise deforms. Therefore the syringe of the invention is advantageous in that it helps maximizing the storage time period over which the dental material can be stored in the syringe without significant alterations.

In one embodiment the syringe comprises a cartridge having a cartridge front end with a first dispensing nozzle and a second dispensing nozzle. The syringe of this embodiment may be used to store the dental material in the form of two separate components. The syringe further preferably comprises a closure for openably closing the first and second dispensing nozzle. The closure comprises a cap, as well as a first seal and a second seal. The cap, and thus preferably the closure, is telescopically placeable on the cartridge, in particular on the cartridge front end. One of the closure and the cartridge has a first magnet for establishing a magnetic attraction between the closure and the cartridge. For example, the cartridge may have a first magnet for establishing a magnetic attraction between the closure and the cartridge. In a situation in which the closure is placed on the cartridge front end, the first and second seal are arranged between the cap and the first and second dispensing nozzle, respectively, with the closure and the cartridge being positionable in a sealing position in which the first and second seal space the cap and the cartridge front end away from each other against a magnetic attraction that urges the cap and the cartridge toward each other.

Preferably the closure is retained on the cartridge in the sealing position by magnetic attraction that urges the closure onto the cartridge so that the first seal (or the first and second seal) are pressurized by magnetic force (a force that results from the magnetic attraction) independent of a shrinkage (or compression set) the first seal (or the first and second seal) may exhibit over time.

The wording "the first and second seal space the cap and the cartridge front end away from each other against a magnetic attraction that urges the cap and the cartridge toward each other" further means that (in absence of a third or further seal) if the first and second seal would not be present, the cap would move further toward the cartridge front end. In other words (in absence of a third or further seal) only the presence of the first and second seal prevent the cap and the cartridge front end to further move toward each other.

In an embodiment the first and second seal are resilient. The first and second seal may be made of rubber or an elastomeric polymer. Although rubber generally provides for a minimized compression set (deformation under mechanical load over time) the invention enables the use of elastomeric polymers for the first and second seal. Many elastomeric polymers exhibit a higher compression set than rubber and therefore may cause leakage over time if used as a sealing material. The use of elastomeric polymers for the first and second seal is enabled due to the self-resealing effect provided by the present invention. In comparison to rubber, elastomeric polymers may be injection molded at minimized molding cycles and thus at minimized production costs. Suitable rubber materials include ethylene propylene rubber (EPR), styrene butadiene rubber (SBR), ethylene propylene diene monomer rubber (EPDM). Suitable elastomeric polymers include styrene-butadiene-styrene block copolymer (SEBS) and thermoplastic polyurethane (TPU).

In an embodiment the cap and the cartridge front end are telescopically slidable relative to each other (in particular on each other). In particular in a situation in which the closure and thus the cap, is placed on the cartridge front end, the closure or cap is telescopically slidable on the cartridge front end.

In an embodiment the other one of the closure and the cartridge comprises a second magnet or ferromagnetic material. Examples of ferromagnetic materials include Fe, Ni, Co, alloys such as AlNiCo, SmCo, $Ni_{80}Fe_{20}$, and combinations thereof. The first and second magnet or ferromagnetic material in combination may form a magnetic coupling that provides for the magnetic attraction between the closure and the cartridge. The first magnet may be arranged within the cartridge, in particular within the cartridge front end. Further, second magnet or ferromagnetic material may be arranged within the closure, in particular within the cap.

Preferably, the magnetic attraction is determined such that the cap and the cartridge are caused to slide toward each other within an attraction range from the sealing position. The attraction range is defined by a distance from the sealing position at which the cap and the cartridge are still caused to move toward each other. This means that the cap and the cartridge are not caused to move toward each other outside the attraction range. At a distance just outside the attraction range some magnetic attraction may be still present, but friction forces may hinder the cap and the cartridge to move toward each other. The attraction range can be determined by design of the cap and the cartridge, and by selection of the at least first magnet (or by selection of the first and second magnet). The first and second magnet are preferably oriented with their magnetic poles such that they attract each other in a situation in which the closure is placed on the cartridge front end.

In one embodiment the first magnet comprises a ferromagnetic material such as a neodymium magnet. Further, the second magnet may comprise the same or different ferromagnetic material such as a neodymium magnet. The first and second magnet may have a prismatic shape. Exemplary dimensions of the first and second magnet comprise a base area of 5 mm×5 mm with a height that ranges from 2 mm to 5 mm. Preferred types of the first and second magnet are NdFeB N52 or NdFeB N54

In one embodiment the attraction range is at least 15 mm. The attraction range may be in particular at least 10 mm, or within a range of 5 mm to 20 mm. As described above the attraction range can be determined by design of the components and selection of the materials.

In one embodiment the cap is cup-shaped or generally cup-shaped. The cap may particularly comprise a bottom wall from which a side wall protrudes. In a situation in which the closure is placed on the cartridge front end the side wall is preferably mated with the cartridge front end and at least the first seal is (or the first and second seal are) arranged between the bottom wall and the first dispensing nozzle (or between the bottom wall and the first and second dispensing nozzle). Preferably the first seal, or the first and second seal limit a travel of the closure on the cartridge front end in a direction of the closure and the cartridge front end toward each other.

In one embodiment the cartridge comprises at least a first chamber for containing the flowable material. The first chamber preferably opens into the first dispensing nozzle. The cartridge may comprise a first and second chamber for containing the flowable material. The first and second chamber preferably each open into the first and second dispensing nozzle, respectively. The syringe may further comprise at least a first piston within the first chamber for advancing the flowable material toward the first dispensing nozzle. Further, the syringe may comprise a first piston within the first chamber and a second piston within the second chamber for advancing the flowable material toward the first and second dispensing nozzle, respectively. For advancing the flowable material toward the first dispensing nozzle, preferably the first and second piston are displaceable relative to the first and second chamber, respectively, in a dimension parallel to the longitudinal axis.

It is noted that the present invention may be used also with a syringe for storing and dispensing a three or more component flowable (for example dental) material. Such a syringe accordingly may have a third or further dispensing nozzle, a third or further seal, a third or further chamber and a third or further piston.

The first and second seal may be formed by one contiguous common seal. The first and second seal in this case are provided portions of the common seal. Thus, the first and second seal may be monolithically formed in one piece.

In one embodiment the cartridge front end and the closure are rotatable relative to each other in a situation in which the cartridge front end and the closure are mated with each other. In particular, the cartridge front end and the closure may be rotatable relative to each other in a situation in which the cartridge front end and the closure are mated in the approximate position (or outside the sealing position). For example, the cap may form a cylindrical receptacle for receiving the cartridge front end therein. In this embodiment the first magnet may be arranged in offset from the longitudinal axis. Further, preferably the second magnet may be arranged in offset from the longitudinal axis. The first and second magnet may be arranged at the same or generally the same distance perpendicular of the longitudinal axis. Therefore, once the closure and the cartridge front end are mated in the approximate position the magnetic attraction provided by the first and second magnet causes the closure and the cartridge front end to move toward each other along the longitudinal axis and in addition to rotationally align relative to each other about the longitudinal axis. The closure and the cartridge front end typically rotationally align such that the closure and the cartridge front end assume a position in which the distance between the first and second magnet are minimized. Accordingly typically the closure and the cartridge front end automatically rotate toward each other (by virtue of the magnetic attraction) until the first and second magnet are positioned on an axis that is parallel to the longitudinal axis but offset therefrom. Therefore the closure can be prevented from being mated in a misaligned manner. This further helps minimizing the risk of cross-contamination between two components stored in the syringe because it can be ensured that the first and second seal automatically realign with the first and second dispensing nozzle, respectively. Thus, any residual flowable material of the first dispensing nozzle eventually present on the first seal may not get into touch with the second dispensing nozzle and any residual flowable material of the second dispensing nozzle eventually present on the second seal may not get into touch with the first dispensing nozzle. In this embodiment the first magnet may be formed by two magnets that are arranged angularly offset by 180 degrees from each other about the longitudinal axis. The second magnet may also be formed by two magnets that are arranged angularly offset by 180 degrees from each other about the longitudinal axis. More than two magnets that distributed (for example, uniformly distributed) about the longitudinal axis may be used for the first and second magnet.

In one embodiment the cap is molded from a first plastic material and the cartridge is molded from a second plastic material.

In an embodiment (a) the first magnet is arranged within the cartridge with a portion of the second material being arranged between the first magnet and the cap. In an alternative embodiment (b) the first magnet is arranged within the cap with a portion of the first material being arranged between the first magnet and the cartridge.

In the embodiment (a) the first magnet is arranged within the cartridge and is surrounded, preferably entirely surrounded, by the second plastic material. In the embodiment (b) the first magnet is arranged within the cap and is surrounded, preferably entirely surrounded, by the first plastic material.

In a further embodiment the syringe comprises a lever for portion-wise expelling the flowable material. The lever is preferably pivotally connected to the cartridge. The syringe may be adapted such that pivoting of the lever causes the first piston, or the first and second piston to move toward the first and second dispensing nozzle, respectively. The first and second piston may be connected and may form one common plunger arrangement. The plunger arrangement may have a toothing for engagement with a pawl that is driven by the lever for advancing the plunger arrangement toward the first and second dispensing nozzle.

In a further embodiment the syringe comprises the flowable material, preferably a dental material, for example a hardenable dental filling material.

In one embodiment the cap and the cartridge front end are sized to provide a play between the cap and the cartridge front end. The play is preferably dimensioned to enable the cap to skew relative to the cartridge allowing the cap to compensate a tolerance between the cap and the first and second dispensing nozzle and thus for the first and second seal to equally seal the first and second dispensing nozzle.

DETAILED DESCRIPTION

Figure 1:
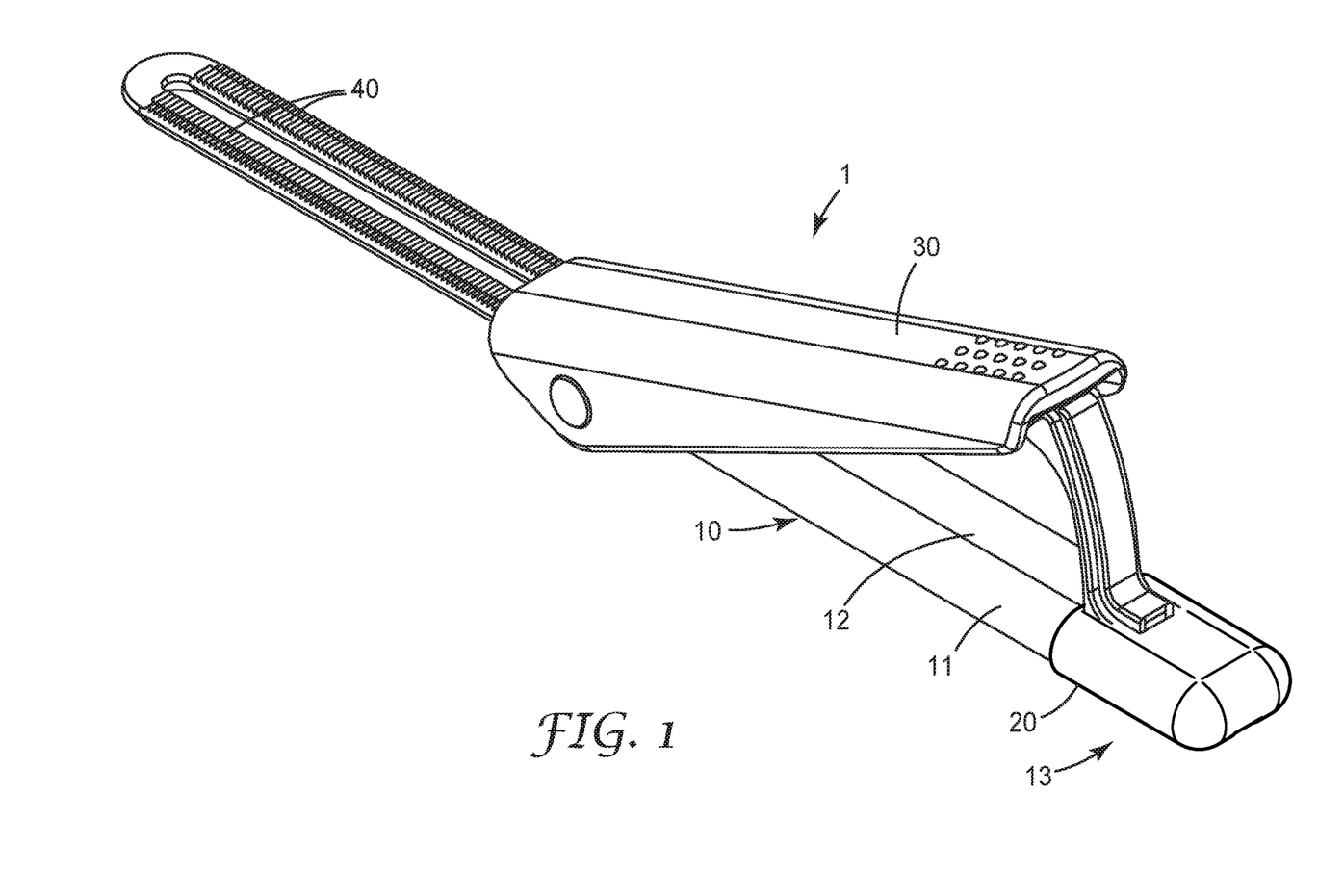
FIG. 1 is a perspective view of a syringe according to an embodiment of the invention.

FIG. 1 shows one example of syringe 1 for dispensing a flowable material in accordance to the invention. The syringe 1 comprises a cartridge 10 that has a first and a second barrel 11, 12 that form a first and a second chamber (visible in FIG. 2), respectively. The syringe 1 is configured for storing and dispensing two components of the flowable material, one component in each of the first and second chamber. The cartridge 10 has a cartridge front end 13 on which a closure 20 is placed. The closure 20 closes a first and second dispensing nozzle (visible in FIG. 2). For dispensing the two components, the closure 20 can be removed for opening the first and second dispensing nozzle. The flowable material can be prepared for use by mixing the two components. In the example the syringe 1 is configured for dispensing the two components side by side and separate from each other. Thus, the components may be dispensed on a mix pad where they can be manually mixed to form the flowable material. In the alternative a mixer (not shown), in particular a static mixer, may be mounted on the cartridge front end 13. In this case the two components, dispensed from the cartridge 10, flow through the mixer where they are merged and mixed and exit the mixer as the flowable material.

In the example the syringe 1 has a lever 30 which serves for (stepwise) advancing a plunger arrangement 40 for dispensing the flowable material. The plunger arrangement 40 has a first and a second piston that are connected and advanced simultaneously. The function of the lever and the plunger arrangement is described in further detail in WO 97/27000 A2. It is noted that in another example the syringe may have a cartridge that has a fingerplate and one or two (separate or connected) pistons, provided with a thrust plate. Such a syringe is typically operated by urging the piston(s) forward by use of the fingerplate and thrust plate. Accordingly a lever is typically not provided in such an example. Further, the syringe may only have a single chamber for a single component flowable material, although in the Figures a syringe for a two component flowable material is illustrated.

Figure 2:
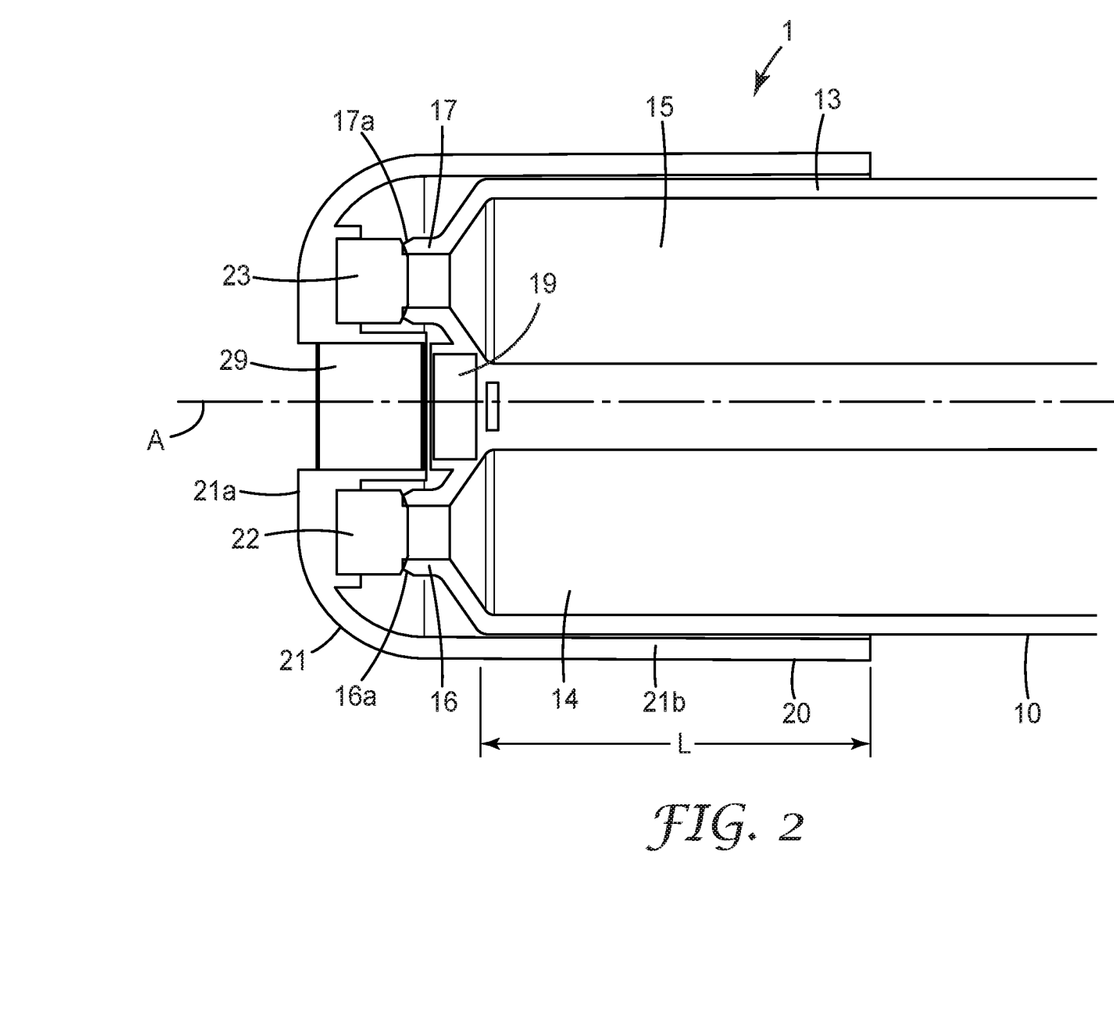
FIG. 2 is a cross-sectional partial view of the syringe shown in FIG. 1.

FIG. 2 shows a cross-sectional portion of the syringe 1 illustrated in FIG. 1. Accordingly the embodiment shown in FIGS. 1 and 2 are the same and thus technically identical, although illustrated in different ways.

The syringe 1 has a first chamber 14 and a second chamber 15. The first and second chamber 14, 15 are formed by the cartridge 10 of the syringe 1. The cartridge 10 at the cartridge front end 13 comprises a first dispensing nozzle 16. The first dispensing nozzle 16 forms a first dispensing opening 16a. Further, the cartridge 10 at the cartridge front end 13 comprises a second dispensing nozzle 17. The second dispensing nozzle 17 forms a second dispensing opening 17a.

The closure 20 is illustrated in a situation in which the closure 20 closes or seals the first and second dispensing nozzle 16, 17. The closure 20 comprises a cap 21, a first seal 22 and a second seal 23. The first and second seal 22, 23 are made of a resilient material, such as rubber or a thermoplastic elastomer.

The cartridge 10 extends along a longitudinal axis A. The first and second chamber 14, 15 extend at a uniform cross-section (in the example a circular cross-section) in a dimension parallel to the longitudinal axis A. Other cross-sections are possible, for example D-shaped or oval cross-sections.

The closure 20, in particular the cap 21, is telescopically placed on the cartridge front end 13. This means that the cartridge front end 13 is received within the closure 20 and that the closure 20 and the cartridge front end 13 are slidably displaceable relative to each other. In particular, the closure 20 and the cartridge front end 13 are slidably displaceable relative to each other along the longitudinal axis A. Further, the closure 20 and the cartridge front end 13 guide each other for a displacement along the longitudinal axis. The guidance is such that the cartridge 10 and the closure 20 are restricted in a movement laterally of the longitudinal axis A and from a rotation in planes parallel to the longitudinal axis A. A slight rotation may be permitted to allow skewing of the cap at a restricted skewing angle. The skewing angle is measured between opposite angles symmetrically to the longitudinal axis, and is preferably less than 5 degrees.

The closure 20 is particularly illustrated at a sealing position relative to the cartridge 10. In the sealing position the first and second seal 22, 23 seal are urged by the cap 21 onto the first and second dispensing nozzle 16, 17 and thus seal the first and second dispensing openings 16a, 17a. The first and second seal 22, 23 seal are urged by the cap 21 onto the first and second dispensing nozzle 16, 17 in consequence of magnetic attraction between the cap 21 and the cartridge front end 13, as described in more detail below.

In the sealing position the first and second seal 22, 23 space the cap 21 and the cartridge front end from each other. This means that in the sealing position the cap 21 is displaced as far in a direction toward the cartridge front end 13 that the first and second seal 22, 23 stop any further displacement of the cap 21 and the cartridge front end 13 relative to each other in that direction. From the sealing position, the cap 21 and the cartridge front end 13 are, however, enabled to be displaced in a direction away from each other. The cap 21 (or the closure 20) and the cartridge front end 13 are displaceable away from the sealing position, for example by a user pulling the closure 21 and the cartridge away from each other against magnetic attraction. Thus the first and second dispensing nozzle 16, 17 can be opened for dispensing the flowable material.

The closure 20 and the cartridge front end 13 in the sealing position telescopically overlap over a guide length L. The cap 21 of the closure therefore is cup-shaped and comprises a bottom wall 21a from which a side wall 21b protrudes. The side wall 21b is dimensioned so that a portion of the cartridge front end 13 can be slidably inserted into the cap 21. Further, the guide length L is defined by a portion of the syringe 1 over which the cap 21 and the cartridge front end 13 slidably guide each other along the longitudinal axis A. The fit between the cap 21 and the cartridge front end 13 is designed so that a stick-slip effect during sliding is avoided. The skilled person is aware of the potential stick-slip effect between two slidably fitted components (also known as the "drawer effect" or "Schubladeneffekt") and design rules for preventing such a stick-slip effect.

The closure 20 and the cartridge 10 are magnetically coupled. This means that the closure 20 and the cartridge 10 are in magnetic attraction with each other. In the example the cartridge front end 13 comprises a first magnet 19. The first magnet 19 is arranged between the first and second dispensing nozzle 16, 17 and is entirely embedded within the cartridge front end 13. A second magnet 29 is arranged within the cap 21. The second magnet 29 is arranged in a center of a cross-section of the cap 21 on a plane perpendicular to the longitudinal axis A. Accordingly, in the sealing position the first and second magnet 19, 29 are each located symmetrically on the longitudinal axis A of the syringe. The first and second magnet 19, 29 are selected and arranged to attract each other. Further, the first and second magnet 19, 29 are further selected and designed such that the closure 20 and the cartridge 10 slide toward each other by magnetic attraction in any position along the guide length L. This can be achieved by selecting an appropriate loose fit between the cap 21 and the cartridge front end 13 (accounting for avoiding any stick-slip effect—see above) and by providing appropriate magnets or ferromagnetic materials, in the example neodymium magnets. The magnets are particularly designed at a sufficient size and shape to achieve the desired magnetic attraction. In the example the first and second magnet 19, 29 are each neodymium magnets having a prismatic (or cylindrical) shape. In the example the first magnet 19 has dimensions of 5 mm×5 mm×2 mm, and the second magnet 29 has dimensions of 5 mm×5 mm×5 mm. The guide length between the closure 20 and the cartridge front end 13 in the example is 20 mm. The magnetic attraction provided between the first and second magnet 19, 29 in the example ranges over at least 18 mm so that once the closure 20 is placed on the cartridge front end 13 at a telescopic overlap of 2 mm, the closure 20 is automatically pulled onto the cartridge front end 13 by magnetic attraction.

The first and second magnet 19, 29 further are spaced in the sealing position. Further the cap 21 and the cartridge front end 13 are spaced in the sealing position. Therefore in case the first and second seal 22, 23 reduce in dimension (for example due to long-term compression deformation) the cap 21 can slide to a new sealing position in which the first and second seal 22, 23 are still sealing the first and second dispensing openings 16a, 17a. Accordingly the syringe 1 is configured for self-re-adjusting (or self-re[[f]]sealing) the closure 20 and the cartridge 10 relative to each other in case dimensional changes of the first and second seal 22, 23 occur.

Figure 3:
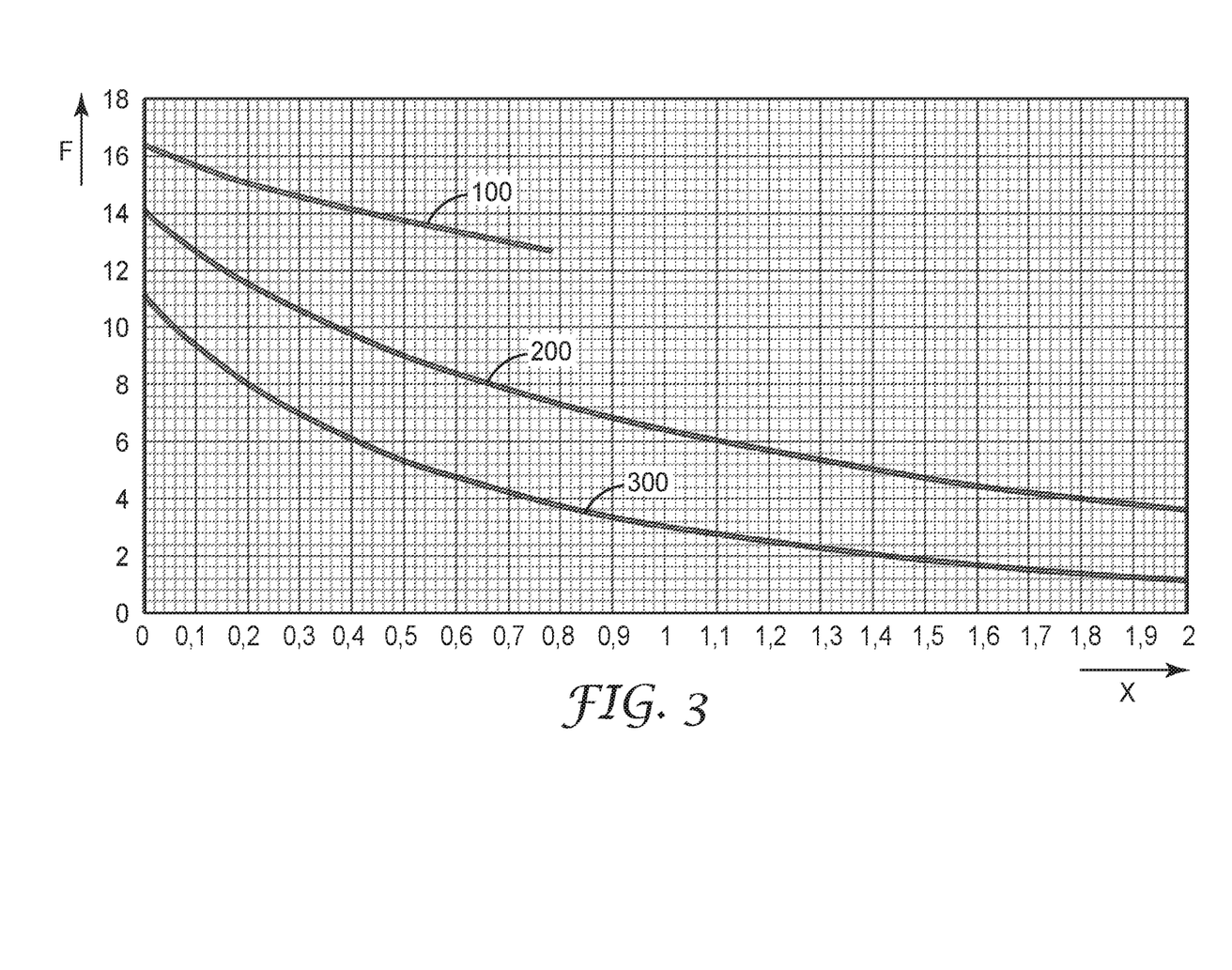
FIG. 3 is a diagram illustrating magnetic attraction forces for different types of magnetic couplings as they may be used with the invention.

FIG. 3 is a diagram representing magnetic attraction forces F (in Newton) over a distance X (in millimeters) between two magnets or between a magnet and a magnetic metal part. According to the invention the magnets (or magnet/metal) are selected to establish a magnetic attraction force that is sufficient for moving the closure 21 and the cartridge front end 13 in a self-acting manner. This means that the magnetic coupling (meaning the combination of magnets or the magnet/metal combination) is preferably selected so that the resulting magnetic attraction force is greater than a slide friction force between the closure 21 and the cartridge front end 13. Further, according to the invention the magnetic coupling is preferably selected such that the closure 21 and the cartridge front end 13 (when telescopically mated) move toward each other in a self-acting manner at a position outside the sealing position. An attraction range defines a position in which the closure 21 and the cartridge front end 13 are arranged at a maximum distance from the sealing position in which they still move toward each other in a self-acting manner. In the example the attraction range corresponds to the guide length or at least 60% to 80% of the guide length. Hence, a closure that is placed on the cartridge front end but not placed in the sealing position id automatically pulled into the sealing position. This helps ensuring that the syringe of the invention self-closes even if the closure is not fully placed in the sealing position. Thus, the flowable material stored in the syringe is prevented from premature altering, for example premature drying or hardening.

By way of example, the diagram illustrates three curves 100, 200 and 300. Curve 100 represents attraction forces F between two neodymium magnets of the type NdFeB N52 of the sizes 5 mm×5 mm×2 mm (5 mm×5 mm square-shaped base area, 2 mm high) over a distance X at which the magnets are spaced. Curve 200 represents attraction forces F between two neodymium magnets of the type NdFeB N45 of the sizes 5 mm×5 mm×5 mm (cube-shaped) over a distance X at which the magnets are spaced, and Curve 300 represents attraction forces F between a neodymium magnet of the type NdFeB N45 of the size 5 mm×5 mm×5 mm (cube-shaped) and a steel part of the type ST37 of the size 5 mm×5 mm×5 mm (cube-shaped) over a distance X at which the magnets are spaced. For all curves 100, 200, 300 the measured distance X corresponds to the spacing or gap between the two magnets. As shown the magnetic coupling represented by curve 100 exhibits the greatest attraction forces F and the least drop of the attraction forces over the distance x. Therefore a pair of neodymium magnets N52 or N45 may be used for providing a maximized attraction range between the closure and the cartridge front end of a syringe of the invention as well as a maximized sealing force.

What is claimed is:

1. A syringe for dispensing a flowable material, comprising a cartridge having a longitudinal axis A, a cartridge front end with a first dispensing nozzle and a second dispensing nozzle, and a closure for openably closing the first dispensing nozzle and the second dispensing nozzle, wherein the closure comprises a cap a first seal and a second seal, wherein the cap is telescopically placeable on the cartridge front end, wherein one of the closure and the cartridge has a first magnet and the other of the closure and the cartridge comprises a second magnet or ferromagnetic material for establishing a magnetic attraction between the closure and the cartridge, and wherein in a situation in which the closure is placed on the cartridge front end, the first seal is arranged between the cap and the first dispensing nozzle and the second seal is arranged between the cap and the second dispensing nozzle, with the closure and the cartridge being positionable in a sealing position in which the first and second seals space the cap and the cartridge front end away from each other against a magnetic attraction that urges the cap and the cartridge toward each other, and wherein, in the sealing position, the first and second magnets are each arranged at a center of a cross-section of the cap between the first and second dispensing nozzles on a plane perpendicular to the longitudinal axis A.

2. The syringe of claim 1, wherein the cap and the cartridge front end are telescopically slidable relative to each other, wherein the magnetic attraction is determined such that the cap and the cartridge are caused to slide toward each other within an attraction range from the sealing position.

3. The syringe of claim 2, wherein the attraction range is at least 15 mm.

4. The syringe of claim 1, wherein the cap is cup-shaped and comprises a bottom wall from which a side wall protrudes, wherein in a situation in which the closure is placed on the cartridge front end the side wall is mated with the cartridge front end and the first seal is arranged between the bottom wall and the first dispensing nozzle.

5. The syringe of claim 1, wherein the cartridge comprises a first chamber for containing a portion of the flowable material and a second chamber containing a remaining portion of the flowable material, wherein the first chamber opens into the first dispensing nozzle, and the second chamber opens into the second dispensing nozzle.

6. The syringe of claim 5, further comprising a first piston within the first chamber for advancing the flowable material toward the first dispensing nozzle and a second piston within the second chamber for advancing the flowable material toward the second dispensing nozzle.

7. The syringe of claim 1, wherein the cap is molded from a first plastic material and the cartridge is molded from a second plastic material, and wherein:
   (a) the first magnet is arranged within the cartridge with a portion of the second material being arranged between the first magnet and the cap;
   or
   (b) the first magnet is arranged within the cap with a portion of the first material being arranged between the first magnet and the cartridge.

8. The syringe of claim 7, wherein:
   (a) the first magnet is arranged within the cartridge and being surrounded by the second plastic material;
   or
   (b) the first magnet is arranged within the cap being surrounded, by the first plastic material.

9. The syringe of claim 1, wherein each of the first and second magnet comprise neodymium magnets.

10. The syringe of claim 1, comprising a lever for portion-wise expelling the flowable material.

11. The syringe of claim 1, wherein the flowable material comprises a dental material.

12. The syringe of claim 10, wherein the cap and the cartridge front end are sized to provide a play between the cap and the cartridge front end, which enables the cap to skew relative to the cartridge allowing the cap to compensate for a tolerance between the cap and the first and second dispensing nozzle and thus for the first and second seal to equally seal the first and second dispensing nozzle.

* * * * *

UNITED STATES PATENT AND TRADEMARK OFFICE
CERTIFICATE OF CORRECTION

PATENT NO. : 11,806,204 B2
APPLICATION NO. : 17/309241
DATED : November 7, 2023
INVENTOR(S) : Marc Peuker Page 1 of 1

It is certified that error appears in the above-identified patent and that said Letters Patent is hereby corrected as shown below:

In the Claims

<u>Column 9</u>
Line 53, Claim 1, insert --,-- between "a cap" and "a first seal".

Signed and Sealed this
Thirteenth Day of January, 2026

John A. Squires
*Director of the United States Patent and Trademark Office*